United States Patent [19]

Kluger et al.

[11] 4,381,265

[45] Apr. 26, 1983

[54] AROMATIC NITRILE-CONTAINING COMPOUNDS USEFUL AS DYESTUFF INTERMEDIATES

[75] Inventors: Edward W. Kluger, Pauline; Joe T. Burchette, Mayo, both of S.C.

[73] Assignee: Milliken Research Corporation, Spartanburg, S.C.

[21] Appl. No.: 286,731

[22] Filed: Jul. 27, 1981

[51] Int. Cl.³ .......................................... C07C 121/78
[52] U.S. Cl. .................................................. 260/465 E
[58] Field of Search ................................... 260/465 E

[56] References Cited

U.S. PATENT DOCUMENTS 2,326,721 8/1943 Bruson .................. 260/465 E X
3,438,967 4/1969 Basel et al. ................. 260/465 E

*Primary Examiner*—Dolph H. Torrence
*Attorney, Agent, or Firm*—H. William Petry; Terry T. Moyer

[57] ABSTRACT

Aromatic nitrile-containing compounds are provided of the formula:

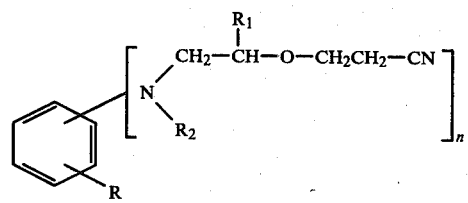

where n is 1 or 2; R is selected from H, Cl, Br, $NO_2$, a lower alkyl group containing from 1 to about 4 carbon atoms, and a lower alkoxy group containing from 1 to about 4 carbon atoms; $R_1$ is selected from H and $CH_3$; and $R_2$ is selected from $CH_2CH_2CN$, an alkyl group containing from 1 to about 6 carbon atoms and:

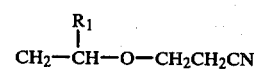

where $R_1$ has the value given above.

11 Claims, No Drawings

AROMATIC NITRILE-CONTAINING COMPOUNDS USEFUL AS DYESTUFF INTERMEDIATES

The present invention relates to aromatic, nitrile-containing compounds useful as intermediates in the preparation of epoxy curing agents and as dyestuff intermediates and to a process whereby such compounds may be prepared.

Acrylonitrile and other chemically related, ethylenically unsaturated nitriles have been widely available commercially at least since the end of World War II, and have become accepted as highly versatile chemical intermediates. Chemical reactions employing such compounds may involve the cyano (CN) group alone, the activated double bond (C=C), or even both groups.

While the most commercially important chemical reaction involving acrylonitrile is its polymerization, other known reactions of the double bond group include dimerization to prepare 1,2-dicyanocyclobutane, the Diels-Alder reaction with, for instance, butadiene to prepare Δ-3-tetrahydrobenzonitrile, hydrogenation to make propionitrile, among others.

Another known chemical reaction involving acrylonitrile and its chemically related ethylenically unsaturated nitriles is the cyanoalkylation reaction (more commonly referred to where acrylonitrile is involved as cyanoethylation). The cyanoalkylation reaction involves the reaction of a suitable ethylenically unsaturated nitrile with active hydrogen-containing compounds, thus introducing the cyanoalkyl group into the reacting molecule.

Active hydrogen compounds which have been reported as being suitable for use in this reaction include a variety of amines, amides, alcohols, mercaptans, aldehydes, ketones, esters, inorganic acids, and their salts [American Cyanamid Company, "The Chemistry of Acrylonitrile," Volume V *Cyanamid's Chemical Digest* (New York, NY: Beacon Press, 1951), p. 26].

As to the cyanoalkylation of alcohols and other hydroxy compounds with acrylonitrile, the literature reports a large number of available aliphatic monohydric and polyhydric alcohols, as well as alcohols containing ether, tertiary amino, and other non-reacting groups and phenols. See Table VI on pages 28–29 of the Cyanamid publication.

The list of amines which have been reported to be suitable for the cyanoalkylation reaction is also rather long, including aliphatic, aromatic, and heterocyclic bases. See Table VIII, pages 32–33 of the Cyanamid publication.

While the list of nitrile-containing compounds which have been prepared by the cyanoalkylation reaction is quite long, there remains a demand for novel cyanoalkylated compounds, especially aromatic cyanoalkylated compounds useful as intermediates in the preparation of epoxy curing agents and as dyestuff intermediates. There is also a very substantial need for techniques whereby such compounds may be prepared in high yields by a cyanoalkylation reaction while at the same time avoiding undesired by-product formation such as acrylonitrile polymer formation, etc.

Accordingly, the present invention provides novel, aromatic nitrile-containing compounds useful as dyestuff intermediates and as intermediates in the preparation of aromatic amines which may be commercially attractive as epoxy curing agents.

The aromatic nitrile-containing compounds of the present invention may be represented by the following structural formula:

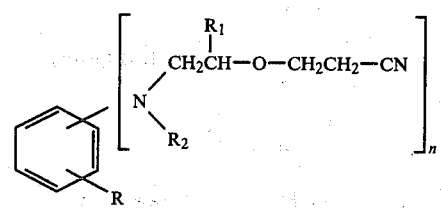

where n is 1 or 2; R is selected from H, Cl, Br, $NO_2$, a lower alkyl group containing from 1 to about 4 carbon atoms, and a lower alkoxy group containing from 1 to about 4 carbon atoms; $R_1$ is selected from H and $CH_3$; and $R_2$ is selected from $CH_2CH_2CN$, an alkyl group containing from 1 to about 6 carbon atoms and:

$$CH_2-\underset{\underset{R_1}{|}}{CH}-O-CH_2CH_2CN$$

where $R_1$ has the value given above.

According to a preferred embodiment of the present invention, n is 1, R is provided in either the ortho or meta position, even more preferably the meta position, relative to the nitrogen atom on the aromatic ring, and $R_1$ is H. Also, according to a preferred embodiment, R may be selected from H, $CH_3$, and Cl. Preferably, $R_2$ may be $CH_2CH_2CN$, lower alkyl, e.g. methyl, ethyl, butyl, or $-CH_2CH_2-O-CH_2CH_2CN$. Examples of most preferred compounds within the scope of the present invention including the following:

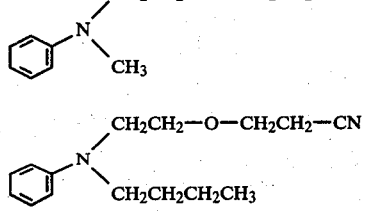

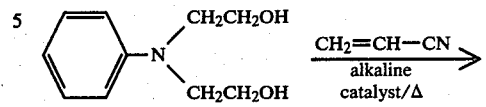

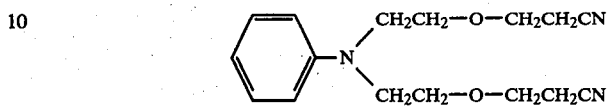

The present invention also relates to a process whereby aromatic, nitrile-containing compounds may be prepared by a cyanoalkoxylation reaction wherein undesired side reactions and undesired polymerization of the ethylenically unsaturated nitrile reactant is avoided or minimized. According to such reaction, an arylalkanolamine may be reacted with an ethylenically unsaturated nitrile in the presence of a lithium catalyst at a temperature of from about 50° C. to about 100° C., preferably about 60° C. to about 80° C., e.g. about 60° C. to about 65° C.

The arylalkanolamine compounds which may be employed as starting materials according to the process of the present invention may be commercially available compounds, or they may be prepared quite conveniently using conventional techniques which will be readily apparent to those skilled in the art. Such compounds include mono-, di-, and higher order arylpolyalkanolamines. Preferred arylalkanolamine compounds which may be employed according to the process of the invention include compounds of the formula:

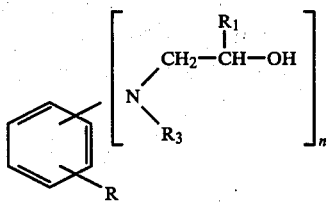

wherein n, R, and $R_1$ have the values given above and $R_3$ is selected from $CH_2-CH_2-CN$, an alkyl group containing from 1 to about 6 carbon atoms and

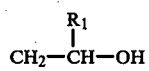

where $R_1$ has the value given above.

A preferred embodiment of the present invention will be described with particular reference to acrylonitrile and phenyldiethanolamine as the starting materials to be employed. It is to be understood, however, that the invention is not to be limited, either to the use of acrylonitrile or to the use of phenyldiethanolamine as the particular starting materials. Other suitable ethylenically unsaturated nitriles which may be employed include, for instance, crotonitrile and methacrylonitrile, to name just a few In accordance with a preferred embodiment, bis-2-cyanoethylphenyldiethanolamine may be produced by the cyanoethylation of phenyldiethanolamine with acrylonitrile either in the presence or the absence of a solvent. The corresponding dinitrile is produced in high yield as shown in the equation below:

The temperature at which the hydroxylpolycyanoethylation occurs may vary widely. Generally, however, the temperature may be within a range of from about 30° C. to about 100° C., and preferably in the range of 50°–80° C. Likewise, the period of time required for the reaction to go to substantial completion may vary widely, such being dependent on the acrylonitrile concentration, alkaline catalyst concentration, solvent, as well as the temperature with which such reaction is carried out. Generally, however, the reaction proceeds to completion when the reactants are contacted at the required temperature for a period of time from about 1 to about 12 hours.

The hydroxylcyanoethylation may be accomplished in the presence of an alkaline catalyst. Typical of such cyanoethylation catalysts are sodium, potassium, and lithium hydroxides. Lithium hydroxide is most preferred. The amount of catalyst employed in the hydroxylcyanoethylation can vary widely. However, the amount of catalyst may be from about 0.025 to about 3 weight percent, preferably from about 0.25 to 1 weight percent.

The hydroxylcyanoethylation may be carried out in the presence or absence of a solvent. When solvent is employed, any suitable solvent which will not interfere with the desired cyanoethylation can be employed, such as cycloaliphatic ethers, e.g. dioxane, tetrahydrofuran, and the like, and higher boiling hydrocarbons, e.g. hexane, cyclohexane, heptane, decane, toluene, xylenes, and the like.

The nitrile-containing compounds of the present invention may have a wide variety of end use applications that will be readily apparent to those skilled in the art. One particularly significant use, however, for the nitrile-containing compounds of the invention is as an intermediate compound which may be further processed by, for instance, hydrogenation of the cyanoalkyl groups to the corresponding amines. Such amines may be particularly useful as epoxy curing agents. In addition to the polyamine end use, the polycyanoalkylarylpolyalkanolamines of the present invention may be used as dyestuff intermediates by coupling, for instance, the corresponding cyanoalkylarylpolyalkanolamine with a wide variety of diazonium salts.

In order to more fully describe the subject matter of the present invention, the following examples are given. Such examples, however, are presented for illustration only and are not to be construed as unduly limiting the scope of the present invention. Unless otherwise indicated, all parts and/or percentages given in these examples are by weight.

EXAMPLE 1

In a 3000-cc three-necked flask equipped with an overhead stirrer, reflux condenser, nitrogen purge, dropping funnel, and thermometer was charged 1005.5 gm (5.6 moles) of phenyldiethanolamine (premelted) along with 3 gm of anhydrous lithium hydroxide. The overhead stirrer was then adjusted to high speed and the flask was preheated to 50° C. with a water bath. Acrylonitrile was then added through the dropping funnel. Over the course of 1.1 hours, a total of 892 gm (16.8 moles) acrylonitrile was added at a rate such that the reaction temperature did not exceed 74° C. The reaction flask was then heated to 65°-70° C. for 12 hours. The reaction contents were cooled to room temperature and made slightly acidic with 85% $H_3PO_4$. The reaction contents were then filtered. The crude filtered reaction product was stripped of all excess acrylonitrile under vacuum (15-30 mm Hg) at a temperature not exceeding 80° C. to give the pale yellow liquid bis-2-cyanoethylphenyldiethanolamine. Liquid chromatography showed the product to be of about 97% purity. The IR, NMR, and GC mass spectra of the product were consistent with bis-2-cyanoethylphenyldiethanolamine. The elemental analysis was also in agreement with this structure:

Calc. for $C_{15}H_{21}N_3O_2$: C, 65.5%; H, 7.6%; N, 15.3%. Found: C, 66.2%; H, 7.4%; N, 14.5%.

EXAMPLE 2

In a 3000-cc three-necked flask equipped with an overhead stirrer, reflux condenser, nitrogen purge, dropping funnel, and thermometer were charged 983.5 gm (5.04 moles) of metatoluidine diethanolamine (premelted) along with 5 gm of anhydrous lithium hydroxide. The overhead stirrer was then adjusted to high speed and the flask was preheated to 50° C. with a water bath. Acrylonitrile was then added through the dropping funnel. Over the course of 2.0 hours, a total of 800 gm (15.1 moles) acrylonitrile was added at a rate such that the reaction temperature did not exceed 80° C. The reaction flask was then heated to 65°-70° C. for 6 hours. The reaction contents were cooled to room temperature and made slightly acidic with 85% $H_3PO_4$. The reaction contents were then filtered. The crude filtered reaction product was stripped of all excess acrylonitrile under vacuum (15-30 mm Hg) at a temperature not exceeding 80° C. to give the pale yellow liquid bis-2-cyanoethylmetatoluidinediethanolamine. Liquid chromatography showed the product to be of about 97.3% purity. The IR, NMR, and GC mass spectra of the product were consistent with bis-2-cyanoethylmetatoluidinediethanolamine.

EXAMPLE 3

In a 3000-cc three-necked flask equipped with an overhead stirrer, reflux condenser, nitrogen purge, dropping funnel, and thermometer was charged 1323.5 gm (6.15 moles) of metachlorophenyldiethanolamine (premelted) along with 6 gm of anhydrous lithium hydroxide. The overhead stirrer was then adjusted to high speed and the flask was preheated to 60° C. with a water bath. Acrylonitrile was then added through the dropping funnel. Over the course of 1.5 hours, a total of 816 gm (15.4 moles) acrylonitrile was added at a rate such that the reaction temperature did not exceed 95° C. The reaction flask was then heated to 65°-70° C. for 6 hours. The reaction contents were cooled to room temperature and made slightly acidic with 85% $H_3PO_4$. The reaction contents were then filtered. The crude filtered reaction product was stripped of all excess acrylonitrile under vacuum (15-30 mm Hg) at a temperature not exceeding 80° C. to give the pale yellow liquid bis-2-cyanoethylmetachlorophenyldiethanolamine. Liquid chromatography showed the product to be of about 96.3% purity. The IR, NMR, and GC mass spectra of the product were consistent with bis-2-cyanoethylmetachlorophenyldiethanolamine.

EXAMPLE 4

In a one-gallon autoclave was charged 1208 gm (6.75 moles) of hydroxyethylethylmetatoluidine, 6 gm of anhydrous lithium hydroxide, and 532 gm (10 moles) of acrylonitrile. The autoclave was sealed and slowly heated to 50° C. until the initial exotherm was over. The reaction was then heated to 65°-70° C. for 6 hours. The reaction contents were cooled to room temperature and made slightly acidic with 85% $H_3PO_4$. The reaction contents were then filtered. The crude filtered reaction product was stripped of all excess acrylonitrile under vacuum (15-30 mm Hg) at a temperature not exceeding 80° C. to give the orange liquid, 2-cyanoethoxyethylethylmetatoluidine. Liquid chromatography showed the product to be about 97.3% purity. The IR, NMR, and GC mass spectra of the product were consistent with 2-cyanoethoxyethylethylmetatoluidine.

EXAMPLE 5

In a one-gallon autoclave was charged 1019 gm (6.75 moles) of hydroxyethylmethylaniline, 3 gm of anhydrous lithium hydroxide, and 532 gm (10 moles) of acrylonitrile. The autoclave was sealed and slowly heated to 50° C. until the initial exotherm was over. The reaction was then heated to 65°-70° C. for 6 hours. The reaction contents were cooled to room temperature and made slightly acidic with acetic acid. The reaction contents were then filtered. The crude filtered reaction product was stripped of all excess acrylonitrile under vacuum (15-30 mm Hg) at a temperature not exceeding 80° C. to give the orange liquid, 2-cyanoethoxyethylmethylaniline. Liquid chromatography showed the product to be about 97.4% purity. The IR, NMR, and GC mass spectra of the product were consistent with 2-cyanoethoxyethylmethylaniline.

What is claimed is:

1. Aromatic nitrile-containing compounds of the formula:

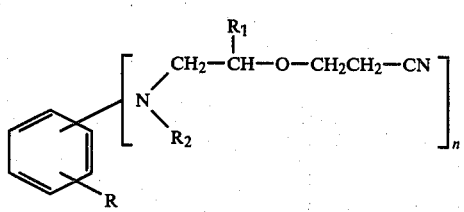

where n is 1 or 2; R is selected from H, Cl, Br, $NO_2$, a lower alkyl group containing from 1 to about 4 carbon atoms, and a lower alkoxy group containing from 1 to about 4 carbon atoms; $R_1$ is selected from H and $CH_3$; and $R_2$ is selected from $CH_2CH_2CN$, and:

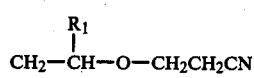

where R₁ has the value given above.

2. The compounds of claim 1 wherein n is 1; and R is provided on the aromatic nucleus in the ortho or meta position relative to the position of the nitrogen atom; and R₁ is H.

3. The compounds of claim 2 wherein R is provided in the meta position.

4. The compounds of claim 3 wherein R is selected from H, CH₃, and Cl.

5. The compounds of claim 4 wherein R₂ is selected from CH₂CH₂CN, and —CH₂CH₂—O—CH₂CH₂CN.

6. A compound of the formula:

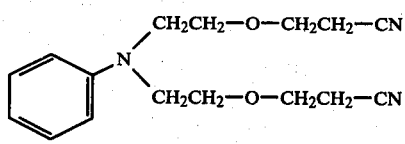

7. A compound of the formula:

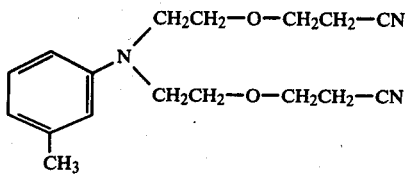

8. A compound of the formula:

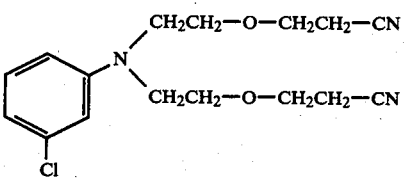

9. A process for preparing an aromatic, nitrile-containing compound which comprises reacting from about a stoichiometric amount to about 1 molar excess of an ethylenically unsaturated nitrile with an arylalkanolamine in the presence of a lithium catalyst at a reaction temperature of from about 50° C. to about 100° C.

10. The process of claim 9 wherein said nitrile is selected from acrylonitrile, crotonitrile, and methacrylonitrile.

11. The process according to claim 9 where said reaction temperature is from about 60° C. to about 80° C.

* * * * *